United States Patent [19]

Corriveau et al.

[11] Patent Number: 5,366,480
[45] Date of Patent: Nov. 22, 1994

[54] SYNTHETIC ELASTOMERIC BUTTRESSING PLEDGET

[75] Inventors: Paul G. Corriveau, Sparta, N.J.; John A. Riley, Brookfield, Conn.

[73] Assignee: American Cyanamid Company, Wayne, N.J.

[21] Appl. No.: 990,367

[22] Filed: Dec. 15, 1992

Related U.S. Application Data

[63] Continuation of Ser. No. 632,555, Dec. 24, 1990, abandoned.

[51] Int. Cl.$^5$ ............................................. A61B 17/04
[52] U.S. Cl. ................................... 606/233; 606/232
[58] Field of Search ............... 606/228, 229, 231, 232, 606/233; 604/365, 358, 362, 372

[56] References Cited

U.S. PATENT DOCUMENTS

| | | |
|---|---|---|
| 818,983 | 4/1906 | Smith . |
| 2,058,318 | 10/1936 | Johnson . |
| 2,264,185 | 11/1941 | Novick . |
| 2,940,247 | 6/1960 | Kirschbaum . |
| 3,625,220 | 12/1971 | Engelsher ......................... 606/233 |
| 3,648,705 | 3/1972 | Lary ................................ 606/233 |
| 3,664,345 | 5/1972 | Dabbs et al. ..................... 606/232 |
| 3,802,438 | 4/1974 | Wolvek ............................ 606/232 |
| 3,825,007 | 7/1974 | Rand . |
| 3,845,772 | 11/1974 | Smith .............................. 606/232 |
| 3,885,570 | 5/1975 | Leveen ............................ 606/233 |
| 3,910,281 | 10/1975 | Kletschka ......................... 606/232 |
| 4,034,850 | 7/1977 | Mandel et al. . |
| 4,164,046 | 8/1979 | Cooley . |
| 4,210,148 | 7/1980 | Stivala ......................... 606/233 X |
| 4,405,324 | 9/1983 | Cruz, Jr. . |
| 4,496,446 | 1/1985 | Ritter et al. . |
| 4,549,545 | 10/1985 | Levy . |
| 4,741,330 | 5/1988 | Hayhurst ......................... 128/92 YF |
| 4,823,794 | 4/1989 | Pierce ............................ 606/232 |
| 4,935,019 | 6/1990 | Papp, Jr. . |
| 5,009,663 | 4/1991 | Broomé ........................... 606/232 |

FOREIGN PATENT DOCUMENTS 2422386 11/1979 France .................... A61B 17/04

OTHER PUBLICATIONS

"Silicones", Encyclopedia of Polymer Science & Technology, N. Bikales, Ed., 1970, 12, pp. 464–569, J. Wiley N.Y.

"Embolization . . . with radiopaque Gelfoam pledgets", D. Kason et al., Journal of Neurosurgery, 1976, 44, pp. 753–756.

". . . Felt Pledgets . . . ", N. Shapira, The Annals of Thoracic Surgery, 1986, 41, pp. 129–221.

"Pericardial Pledgets . . . ", The Annals of Thoracic Surgery, 1986, 42, pp. 601–603.

"Medical Applications", Encyclopedia of Polymer Science & Engineering, 2nd Ed., J. Kroschwitz, Ed., 1987, 9, p. 498, J. Wiley N.Y.

"Resorbable suture support . . . ", J. Vincent et al., and . . . Teflon felt pledgets, H. Borst, The Journal of Thoracic & Cardiovascular Surgery, 1987, 94, pp. 430–433 and 442–443.

Attorney's Dictionary of Medicine & Word Finder "Pledget", J. Schmidt, Ed., 1988, 3, p. 217.

"Silicone Elastomers", Encyclopedia of Polymer Science & Engineering, 2nd Ed., J. Kroschwitz, Ed., 1989, 15, pp. 271–289, J. Wiley N.Y.

Primary Examiner—Peter A. Aschenbrenner
Attorney, Agent, or Firm—Charles F. Costello, Jr.

[57] ABSTRACT

A buttressing pledget is manufactured from a synthetic elastomeric material. The elastomeric material can be nonporous, radiolucent, and/or a silicone rubber. The buttressing pledget can be made radiopaque by the addition of a suitable material, such as barium sulfate. The pledget can be combined with a surgical suture or ligature.

16 Claims, 2 Drawing Sheets

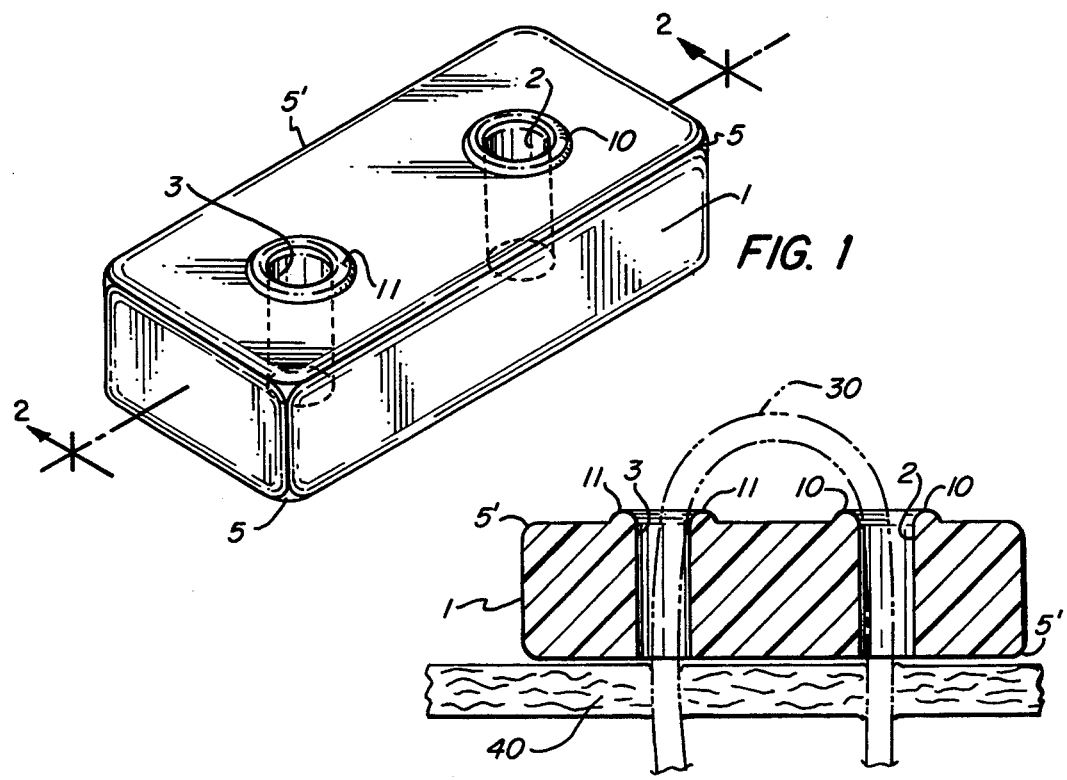
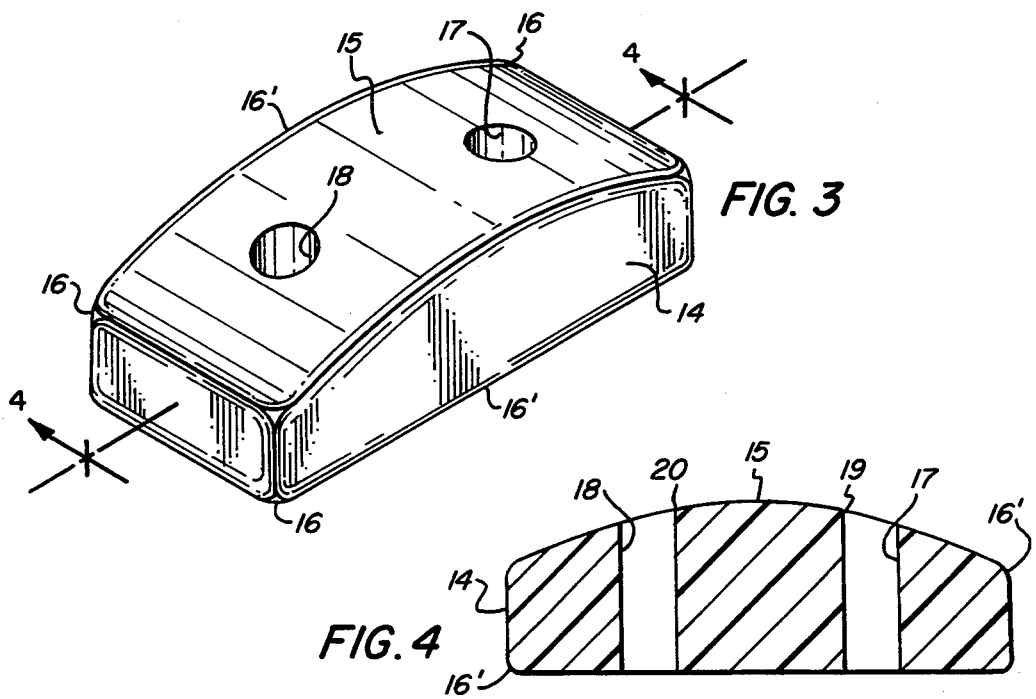

SYNTHETIC ELASTOMERIC BUTTRESSING PLEDGET

This is a continuation of co-pending application Ser. No. 07/632,555 filed on Dec. 24, 1990, now abandoned.

BACKGROUND AND SUMMARY OF THE INVENTION

This invention relates to a buttressing pledget. The buttressing pledget is manufactured from a synthetic elastomeric material. The elastomeric material can be nonporous and/or a silicone rubber. The pledget can also be radiolucent or radiopaque. The buttressing pledget can be made radiopaque by the addition of barium sulfate. This invention also relates to a buttressing pledget in combination with a surgical suture or ligature.

The material used to manufacture a surgical pledget has remained relatively constant in the prior art. Probably to avoid irritation to the tissue, the surgical community prefers a soft, loose, fibrous material. For example, please see U.S. Pat. No. 3,825,007 entitled "Pledgets" which issued Jul. 23, 1974; U.S. Pat. No. 4,405,324 entitled "Absorbent Cellulosic Structures" which issued Sep. 20, 1983; and the definition of pledget in ATTORNEY'S DICTIONARY OF MEDICINE and WORD FINDER, J. Schmidt vol. 3 page P-217, Matthew Bender, N.Y. 1988. The patents are incorporated herein by reference. A coreless braided and woven pledget are also known in the prior art. Both the braided and the woven pledget are manufactured from a Dacron* (DuPont, Del., USA) fiber.

As the surgical community and wound closure industry sought better solutions to health problems, new uses of the pledget began to appear. One of these new uses was a buttress during surgery. This new use gave rise to the buttressing pledget as an article of manufacture, which has achieved a separate status in the art. As an example of the development of the buttressing pledget art, please see U.S. Pat. Nos. 4,164,046 FIG. 6 element 40; 4,549,545; and, generally, 4,823,794. For the packaging of a buttressing pledget in combination with a surgical suture, please see U.S. Pat. No. 4,034,850. These patents are incorporated herein by reference.

The claims in this application are limited to a buttressing pledget. The claimed pledgets can be molded or extruded and have several advantages over the known prior art pledgets. One advantage is that the buttressing pledgets described in this application can be nonfibrous. Because they can be nonfibrous, the problem of exfoliation is essentially eliminated. Another advantage is that the molded or extruded buttressing pledgets can be nonporous. Thus, the problem of tissue ingrowth, which can limit or at least interfere with the wound closure process, is essentially eliminated. For a contrast of these two advantages over the prior art, please see U.S. Pat. No. 4,549,545, column 1 lines 28 to 40 and 46 to 49.

Yet another advantage of a molded or extruded buttressing pledget is that a variety of shapes can be obtained. The availability of various shapes may enhance the efficacy of a known surgical procedure. The shapes described in two dimensions include but are not limited to square, rectangular, round, oval and elliptical, and in three dimensions, the shapes include tubular. Another advantage of a molded or extruded pledget is that it can be manufactured with a more consistent thickness. This advantage can be critical, especially where the pledget is small in size and/or the surgical procedure is major, such as a cardiovascular operation.

Still another advantage is that the buttressing pledget can be manufactured from a radiopaque material. The advantage of a radiopaque material is apparent to the surgical user. For example, in cardiovascular surgery it may be important, if not critical, to know the postoperative location of the pledgets that were used. Knowing the postoperative location, the surgeon or medical technologist can make a prognosis of the patient's wound healing process.

An X-ray photograph, a CAT scan or a similar image can identify the pledget's radiopaque material, and thus show the surgeon or technologist the location of the pledgets. This in turn can indicate that the suturing or stapling technique used by the surgeon is efficacious to the wound healing process.

A further advantage is that the holes formed through a molded or extruded pledget of this invention can be built up around the edges such that the pledget is structurally stronger in these places than the prior art buttressing pledgets. For contrast, please see the edges of the buttressing pledget openings 24, 26 and 42 as shown in U.S. Pat. No. 4,823,794 FIGS. 1 and 2, or the opening in the pledget 16 as shown in U.S. Pat. No. 4,549,545 FIG. 1.

A natural rubber has been disclosed for use as a latex in a neuropledget. The latex is sprayed onto a surface to form a layer. The neuropledget is manufactured by combining the latex layer with an absorbent fibrous material. Please see U.S. Pat. No. 3,825,007, which is more fully cited above. Because the utility disclosed is not a buttressing pledget, because the natural rubber has to be formed into a latex, because the latex is sprayed onto a layer, because the layer is combined with a fibrous composition, this reference is not material to the inventions claimed in this application. Other prior art compositions that have been used to manufacture buttressing pledgets include a Teflon* (DuPont, Del., USA) or polyurethane fibrous mat. Please see U.S. Pat. Nos. 4,549,545 and 4,823,794, which are also cited above.

For a description of a pledget comprising a radiopaque material (Pantopaque*), please see the Journal of Neurosurgery (J. Neurosurg) vol. 44 pages 753–756, 1976. The use of the radiopaque pledget described in this journal article is limited to an arterial embolus and specifically the embolization of an arteriovenous malformation.

For a disclosure of nonpledget medical uses of a silicone rubber, please see Table 3 under the title "Medical Applications" in Encyclopedia Of Polymer Science And Engineering, 2nd Edition, J. Kroschwitz, Ed., vol. 9, page 498, J. Wiley & Sons, NY 1987. It is not seen in any of these uses where there is a teaching or suggestion of a buttressing pledget.

In summary, the surgical community continues to seek a buttressing pledget which will make surgical procedures more efficacious. Please see, e.g., the articles and commentary in The Annals of Thoracic Surgery (Ann Thorac Burg) vol. 41 pages 219–221 and vol. 42 pages 601–603, both published in 1986, and The Journal of Thoracic and Cardiovascular Burgery (J Thorac Cardiovasc Burg) vol. 94 pages 430–433 and 442–443, 1987. These publications are incorporated herein by reference.

BRIEF DESCRIPTION OF THE DRAWINGS

FIGS. 1 and 5 are perspective views of alternative embodiments of the buttressing pledget of this invention;

FIG. 2 is a sectional side view along the plane 2—2 of FIG. 1, showing the in-vivo use of the pledget with a surgical suture strand;

FIG. 3 is a perspective view of another alternative embodiment of the buttressing pledget, having a curvilinear top;

FIG. 4 is a sectional side view along the plane 4—4 of FIG. 3; and

DESCRIPTION OF THE INVENTION

The surgical buttressing pledgets used in this invention are made from injection molded silicone materials. The preparation of this material requires a compounding unit to mix the silicone resins, an injection molding unit, silicon materials, and a mold.

Molds can be in any three dimensional configuration currently adaptable in any molding process. This particular invention recognizes the following configurations which are currently available in teflon felt material, but is not limited only to these shapes: square, rectangular, circular, ovoid and tubular. According to conventional surgical practice, two holes are strategically placed in the pledget for threading of the surgical suture. Pledgets are supplied prethreaded by the manufacturer or can be threaded by the surgeon or nurse prior to use. A tubular shaped pledget is hollow and requires no holes for threading the suture or ligature.

Silicon materials are mixed in the compounding unit under high pressure at a temperature below 10° C. The mix is then injected into the loading part of the molding unit which has been kept at a temperature of approximately 160° C. Vulcanization takes place in the mold within 0.5 to 3.0 minutes, depending on the mold size and configuration. When the vulcanization is complete, the mold is opened and the molded silicon part is manually removed. Deflashing of the silicon part, if necessary, is performed immediately after removal from the mold. For an implantable device such as this, deflashing is performed under magnification.

For a general discussion of the molding or extruding of a heat-cured silicone rubber, which limitation is disclosed in embodiments 13 to 16 above, please see the subtitle "Vulcanization" in Encyclopedia Of Polymer Science And Technology, N. Bikales, Ed., vol. 12 pages 540 to 544, J. Wiley & Sons, NY 1970.

For a description of how to make a surgical element comprising a radiopaque material as disclosed in embodiments 4 and 8, above, and specifically of barium sulfate as disclosed in embodiment 22, above, please see the subheading "Description Of The Preferred Embodiments" and Example 1 in U.S. Pat. No. 4,496,446 entitled "Modification Of Polyglycolic Acid Structural Elements To Achieve Variable In-Vivo Physical Properties", which patent issued Jan. 29, 1985 and is incorporated herein by reference.

Figure 5:
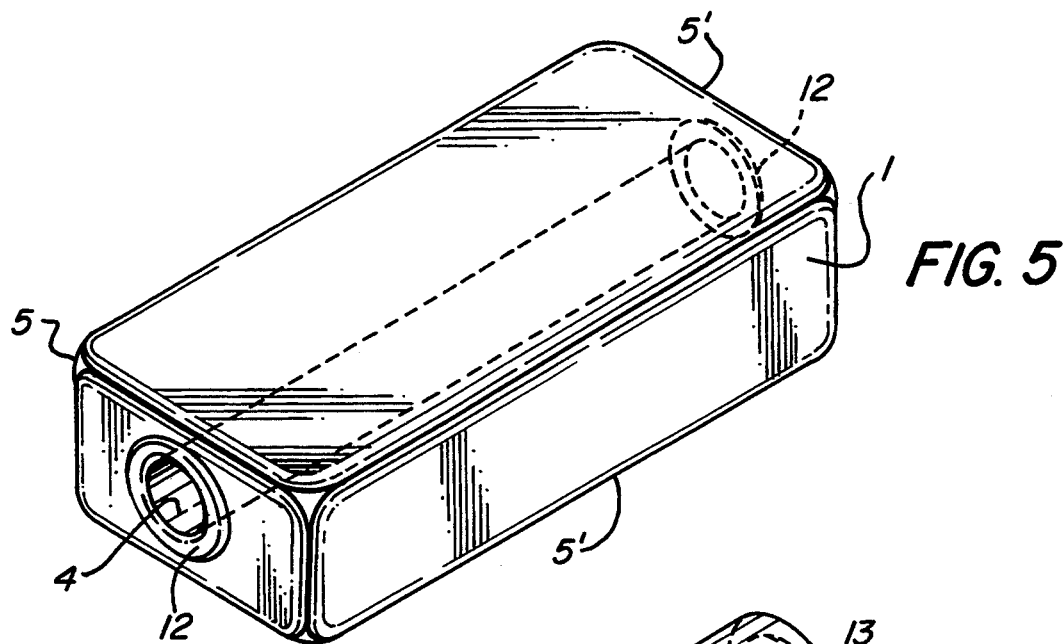

Referring to FIGS. 1 and 5, the molded or extruded buttressing pledget 1 is rectangular in shape. To facilitate the use of the pledget, openings 2 and 3 in FIG. 1, or 4 in FIG. 5 are made through the pledget. As shown in FIGS. 1 and 2, the two openings 2 and 3 are perpendicular to the top and bottom of the pledget 1. However, it is to be understood that another orientation of the openings, for example a diagonal orientation, is possible.

As shown in FIGS. 1, 2 and 5, the corners 5 and edges 5' of the molded or extruded buttressing pledget can be rounded. This reduces or even eliminates the risk that during use, the corner(s) or edge(s) will pierce or in some other way traumatize the tissue being approximated.

Figure 6A:
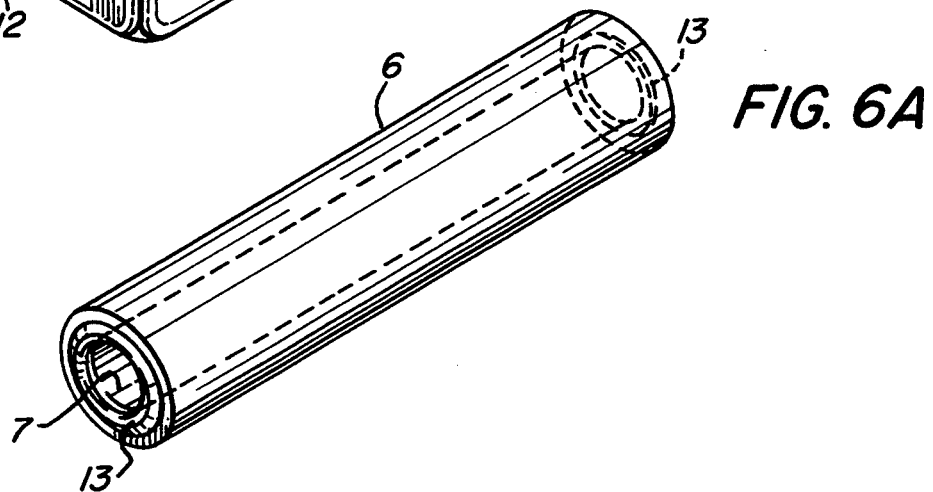
FIGS. 6A and 6B are other alternative embodiments of the buttressing pledget of this invention.
Figure 6B:
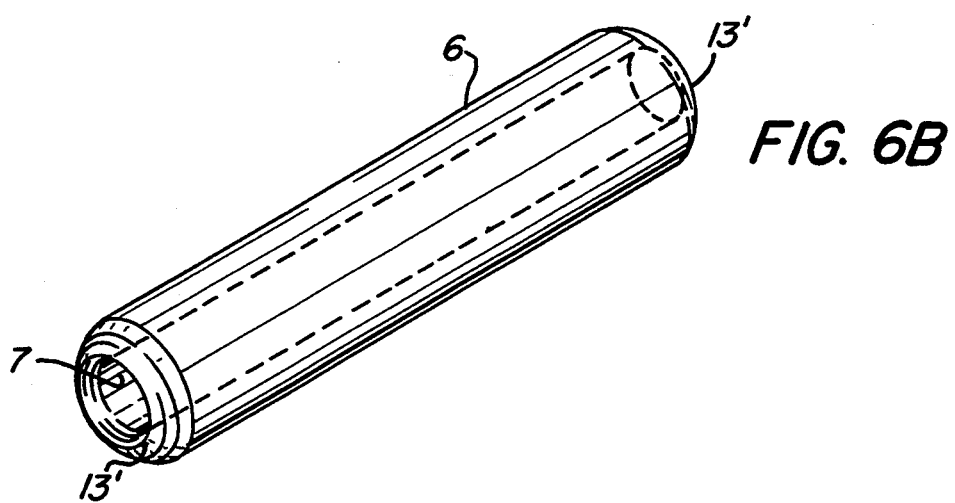

Referring to FIGS. 6A and 6B, the molded or extruded buttressing pledget 6 is tubular in shape. The pledget has an opening 7. Preferably, the opening 7 is parallel to the lengthwise direction of the tubular form. However, it is to be understood that another orientation, for example an opening that is perpendicular or diagonal to the lengthwise direction is also within the scope of this invention.

Referring again to FIGS. 1, 2, and 5, in one embodiment of this invention, a protuberance 10 and 11 at the respective proximal end of each opening 2 and 3 in FIGS. 1 and 2, and a protuberance 12 at either or both the proximal and distal end of the opening 12 in FIG. 5 can be molded directly into the pledget. The term protuberance is intended to be synonymous with the term protrusion. Each of the protuberances (or protrusions) 10 and 11 act as a bumper or reinforcing element. As shown specifically in FIG. 2, the protrusions 10 and 11 increase the margin of error in preventing the surgical suture strand 30 from cutting or tearing through the central portion of the pledget 1 formed between the two openings 2 and 3.

The protuberances as described in this application are thus an advance in the buttressing pledget art. There are at least two related reasons for this advance. First, the strength of the pledget is increased and more specifically, the strength is increased at an area of the pledget that the person skilled in the art knows is the most suspect to structural fatigue or failure. Second, the risk of a tear or other fracture of the pledget by a suture strand during the wound healing process is substantially reduced, if not essentially eliminated.

Referring to FIGS. 6A and 6B, the protrusions shown in FIGS. 1 and 2 can be adapted to other molded shapes. For example, in FIGS. 6A and 6B, the protrusions 13 and 13', respectively, can be at one or both ends of the buttressing pledget.

Another embodiment of a molded or extruded buttressing pledget of this invention is shown in FIGS. 3 and 4. The buttressing pledget 14 has openings 17 and 18. Similar to the rounded corners 5 and edges 5' of FIGS. 1 and 5, this embodiment can also have rounded corners 16 and edges 16'. The concave top 15 is an alternative means for reinforcing the opening(s) described in FIGS. 1, 2 and 5 to above. A description of the concave top 15 as this alternative means is more fully disclosed below.

As shown specifically in FIG. 4, the convex top 15 serves the same function as the protrusions 10 and 11 in FIGS. 1 and 2, or 13 and 13', respectively in FIGS. 6A and 6B. That is, the raised portions 19 and 20 enable the pledget 14 to be reinforced.

A disclosure of how to use the buttressing pledget of this invention is shown in FIG. 2. For conventional use, a surgical suture material 30 is usually prethreaded through the openings 2 and 3 of the pledget 1, as shown. The suture material 30 can be double-armed (that is, have two needles) or single-armed (having a needle at one end). The pledget 1 is then used as a buttress adjacent to the tissue 40, which is being approximated by the single or double-armed surgical suture 30.

Referring again to FIG. 2, it is preferred that the protrusions 10 and 11 only be on a side of the pledget 1 that is opposite to the tissue 40. Thus the trauma to the tissue 40 is not increased because the side of the pledget adjacent to the tissue is relatively flat and smooth. However, it is to be understood that the protrusions 10 and 11 could be molded into either end of the openings 2 and 3.

How to use a pledget as a buttress in a surgical procedure is described in the prior art. Please see, e.g., U.S. Pat. No. 4,823,794, FIGS. 3 to 5 and Ann Thorac Surg 41 FIGS. 1 and 3 to 4, both references being more fully disclosed above under the subheading "Background of the Invention".

For a general description of the synthetic elastomeric material disclosed in embodiments 1, 2 and 8 above, please see the subtitle "Silicone Elastomers" in Encyclopedia Of Polymer Science And Engineering, 2nd Edition, J. Kroschwitz, Editor, vol. 15 pages 271–289, J. Wiley & Sons, NY 1989. Examples of commercial silicone elastomeric compositions include Silplus* (General Electric Co., CT, USA) and Silastic* (Dow Corning Co., Michigan, USA) elastomers.

A molded or extruded buttressing pledget of this invention can be porous. The size of the pores can be controlled by machines and methods known in the prior art. A porous buttressing pledget may be useful in some surgical uses as it probably can provide sites for tissue growth.

For a description of the silicone rubber disclosed in embodiments 5, 6 and 17 above, and heat-stable silicone rubber disclosed in embodiments 7 and 18 to 21, please see the title "Silicones" in Encyclopedia Of Polymer Science And Technology, N. Bikales, Ed., vol. 12 pages 464 to 569, J. Wiley & Sons, NY 1970.

Referring to embodiments 19 to 21, above, it is to be understood that each of these mixtures can be generically described as comprising a trimethylated silica. Referring specifically to embodiment 19, the trimethylated silica mixture is described by Chemical Abstracts Service (hereafter "CAS"; American Chemical Soc., Ohio 43210, USA) Registry No. 68909-20-6; embodiments 20 and 21 are described by CAS Registry No. 68037-59-2. That is, the chemical nomenclature described in these embodiments is intended to be synonymous with the respective CAS Registry number. If there is a discrepancy, the nomenclature disclosed in the CAS Registry number takes precedence and is to be used as the description of the embodiment. These CAS Registry numbers are incorporated herein by reference.

What is claimed:

1. An article of manufacture comprising a buttressing pledget having essentially a rectangular parallelpiped form and two openings, the two openings being essentially parallel to each other and each of said two openings having a proximal end on a first side and a distal end on a second side of the rectangular parallelpiped form, each of said two openings being continuous from the proximal to the distal end, and a raised surface adjacent to at least each of the proximal ends, and in combination with a wound closure device, the buttressing pledger manufactured from a nonporous, synthetic elastomer in combination with a radiopaque material.

2. An article of manufacture comprising a buttressing pledger having essentially a rectangular parallelpiped form and two openings, the two openings being essentially parallel to each other and each of said two openings having a proximal end on a first side and a distal end on a second side of the rectangular parallelpiped form, each of said two openings being continuous from the proximal to the distal end, and a raised surface adjacent to at least each of the proximal ends, the buttressing pledget manufactured from a synthetic elastomeric material and in combination with a radiopaque material.

3. The article of claim 1 wherein the wound closure device comprises at least one filament.

4. The article of claim 3 wherein the wound closure device comprises a monofilament.

5. The article of claim 4 wherein the wound closure device is a surgical suture or ligature.

6. The article of claim 3 wherein the wound closure device is a braided suture or ligature.

7. The article as in any of claims 1–6 comprising a molded buttressing pledget.

8. The article of claim 7 comprising an injection molded buttressing pledget.

9. The article of claim 7 comprising a compression molded buttressing pledget.

10. The article as in any of claim 1–6 comprising an extruded buttressing pledget.

11. The article of claim 3 wherein the nonporous, synthetic elastomer is a silicone rubber.

12. The article of claim 11 comprising a heat-stable silicone rubber.

13. The article of 12 wherein the heat-stable silicone rubber is a mixture comprising 1,1,1-trimethyl-N-(trimethylsilyl)-silanamine, and hydrolysis products of 1,1,1-trimethyl-N-(trimethyl-silyl)-silanamine and silica.

14. The article of claim 13 wherein the mixture comprises 1,1,1-trimethyl-N-(trimethyl-silyl)-silanamine, hydrolysis products of 1,1,1-tri-methyl-N-(trimethylsilyl)-silanamine and silica, a methyl substituted siloxane and a methyl substituted silicone.

15. The article of claim 13 wherein the mixture comprises 1,1,1-trimethyl-N-(trimethyl-silyl)-silanamine, hydrolysis products of 1,1,1-tri-methyl-N-(trimethylsilyl)-silanamine and silica, and a dimethyl, methyl hydrogen siloxane copolymer.

16. The article as in any of claims 1–6, 11 or 12, wherein the radiopaque material is barium sulfate.

* * * * *